(12) United States Patent
Bonnefous (10) Patent No.: US 6,647,135 B2
(45) Date of Patent: Nov. 11, 2003

(54) ULTRASONIC IMAGE PROCESSING METHOD AND SYSTEM FOR DISPLAYING A COMPOSITE IMAGE SEQUENCE OF AN ARTERY SEGMENT

(75) Inventor: Odile Bonnefous, Nogent-sur-Marne (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 550 days.

(21) Appl. No.: 09/732,195

(22) Filed: Dec. 7, 2000

(65) Prior Publication Data

US 2001/0017937 A1 Aug. 30, 2001

(30) Foreign Application Priority Data

Dec. 7, 1999 (EP) .............................. 99403058

(51) Int. Cl.[7] ................................ G06K 9/00
(52) U.S. Cl. ..................... 382/128; 600/455; 128/916
(58) Field of Search ................ 382/128, 130, 382/131; 600/443, 447, 453, 454, 455, 456; 128/916

(56) References Cited

U.S. PATENT DOCUMENTS 5,938,606 A  8/1999 Bonnefous ................. 600/437

FOREIGN PATENT DOCUMENTS

WO  WO9925250  5/1999  ............ A61B/8/08

Primary Examiner—Amelia M. Au
Assistant Examiner—Anand Bhatnagar
(74) Attorney, Agent, or Firm—John Vodopia (57) ABSTRACT

The invention concerns an ultrasonic image processing method for displaying a composite sequence of images of an artery segment with indication of blood flow velocity and wall movements in function of the cardiac cycle, comprising steps of:

forming, at a first rate, a first sequence (131) of blood flow velocity color-coded images and forming, at a second rate, a second sequence (231) of images with wall movement graphics;

and constructing said composite image sequence (361) by determining a first set of temporal markers (n1,n2), related to the cardiac cycle, in the first image sequence as the minimum points of a curve (P(n)) of the number of the colored points per image in function of the image instants, determining a second set of temporal markers (k1,k2), related to the same cardiac cycle, in the second image sequence as the minimum points of a curve (D(k)) of the arterial mean dilation in function of the image instants, and by superposing the first and second image sequences by synchronizing the respective markers of said two sets, and displaying the composite image sequence.

The invention also relates to an ultrasonic examination imaging system carrying out said method.

11 Claims, 4 Drawing Sheets

ULTRASONIC IMAGE PROCESSING METHOD AND SYSTEM FOR DISPLAYING A COMPOSITE IMAGE SEQUENCE OF AN ARTERY SEGMENT

Ultrasonic image processing method and system for displaying a composite image sequence of an artery segment

FIELD OF THE INVENTION

The invention relates to an ultrasonic image processing method for displaying a composite sequence of images of an artery segment with indication of blood flow velocity and wall movements in function of the cardiac cycle, comprising steps of forming, at a first rate, a first sequence of blood flow velocity color-coded images and forming, at a second rate, a second sequence of images with wall movement graphics. The invention also relates to an ultrasonic diagnostic imaging system for carrying out this method.

The invention is used in the field of medical echographic imaging, for providing cardiovascular diagnostic tools for non-invasive study of anomalies of arteries and notably of stenoses. A diagnostic criterion for a stenosis is an abrupt reduction of an artery diameter. Another criterion is the blood velocity in the stenosed zone. Therefore, the medical field has a need for non-invasive means for studying parameters related to arterial wall motion and to blood flow velocity in order to early diagnostic stenosed arteries.

BACKGROUND OF THE INVENTION

A method for displaying a composite sequence of images of an artery segment with indication of color-coded blood flow velocity and arterial wall movement graphics in function of the cardiac cycle is already known from the PCT patent application No WO 99/25250. This method comprises steps of forming, at a first rate, a first sequence of blood flow velocity color-coded images and of forming, at a second rate, a second sequence of images with wall movement graphics and finally of superposing the first and second sequences by synchronizing markers of the starts of the cardiac cycles, previously measured for first and second sequences separately, using an external ECG device. To this end, the ECG measure means is to be applied to the patient in supplement to the ultrasonic measure means. The start and end points of the first and second sequences are further made to coincide by using calculation steps. Then, the composite image sequence is displayed.

As explained before, it is of importance that indications of the actual movements of the walls be available together with the blood flow velocity in order to diagnose stenoses or other diseases. A technical problem resides in the fact that processing a first set of data appropriate to provide arterial wall radial velocity together with processing a second set of data appropriate to provide either Doppler Imaging or CVI is difficult because said first and second sets of data are actually incompatible due to the respective velocities of arterial walls and blood flow, which are in the ratio of one to about fifty. It is the reason why the document cited as state of the art used a system based on supplementary ECG measurements in order to synchronize the first and second sets of data.

SUMMARY OF THE INVENTION

It is a purpose of the invention to provide an image processing method for synchronizing the two sequences of images that are formed from these two sets of data.

This problem is solved by means of a method as claimed in claim 1.

This method offers the advantage that the synchronization is performed using uniquely image processing. This method spares the patient to suffer supplementary ECG measure means and it spares the operator to perform supplementary ECG measures. This method also avoids inaccuracies that appear while making ultrasonic measures and ECG measures coincide. This method also offers the advantage that the arterial wall behavior is made clearly visible together with color-coded indications of the blood flow velocity. So, the physician may easily diagnose stenosis or arterial anomalies.

An ultrasonic diagnostic system having means for carrying out the method is claimed in claim 10, and constitutes a tool for non-invasive diagnostic of arterial wall anomalies.

BRIEF DESCRIPTION OF THE FIGURES

Specific embodiments of the invention will be described in detail hereinafter with reference to the accompanying diagrammatic drawings; therein.

DESCRIPTION OF THE PREFERRED EMBODIMENTS

Figure 1:
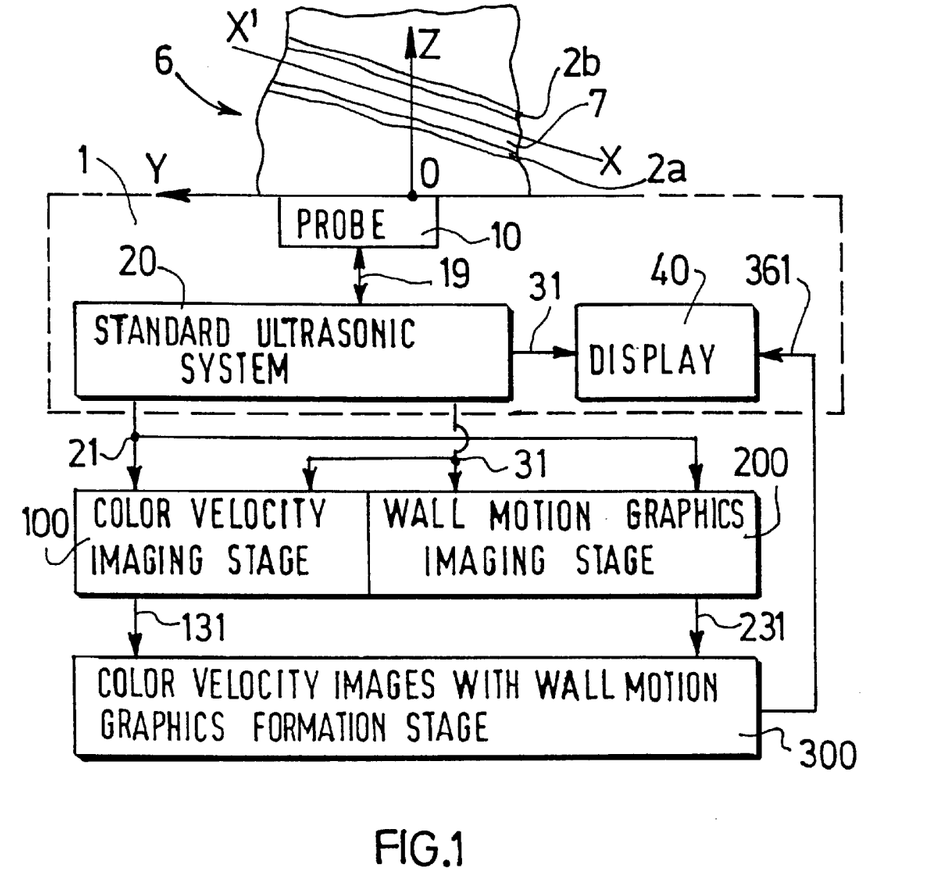
FIG. 1 shows a simplified block diagram of an ultrasonic diagnostic imaging system.

Referring to FIG. 1, an ultrasonic diagnostic imaging system constructed in accordance to the principles of the present invention is shown in a simplified block diagram form. The ultrasonic diagnostic imaging system comprises sub-systems 1, 100, 200, 300 for the construction and display of a sequence of echographic images of an artery, said sequence comprising color-coded blood flow velocity images on which graphic lines representing the arterial wall movements are superimposed. The constructed images of the sequence are 2-D images. A problem solved by the further described method and system is the construction of each sequence image by determining the information appropriate to construct each line of said 2-D image. In the example of embodiment that is described hereafter, the ultrasonic diagnostic imaging system is used as a tool for the examination of an artery located in a medium.

The ultrasonic sub-system 1 comprises a standard ultrasonic system 20 coupled to a probe or scan-head 10 and provided with display means 40. The operation of the standard ultrasonic system 20 involves setting the probe 10 in contact with a medium 6 observed for transmitting, via periodic excitations, ultrasonic signals to said medium in a given direction OZ and for receiving in the same direction OZ, the echoes returned by the obstacles encountered in the medium. The probe 10 may be composed of ultrasonic transducers that are assembled in a linear array having an orientation OY perpendicular to the OZ-axis. A respective transmitting/receiving line corresponds to an acoustic beam generated at a corresponding position.

Figure 2:
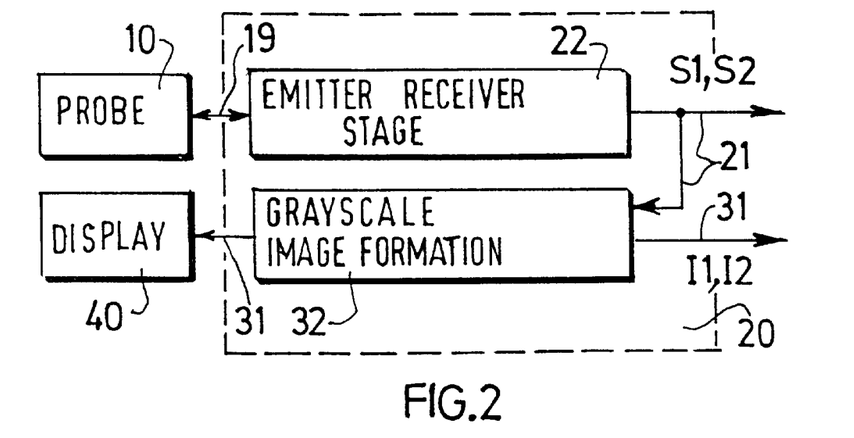
FIG. 2 shows a block diagram of a standard ultrasonic system.

Referring to FIG. 2, the standard ultrasonic system 20, which is connected to the probe 10, includes a transmitter/receiver stage 22 for generating the excitation signals applied to said probe. The probe transducers convert these signals into periodic train of ultrasonic pulse signals supplied with a predetermined recurrent frequency. The returned acoustic signals are received and combined by the transmitter/receiver stage 22 to perform beam formation. Control signals are further supplied by the transmitter/receiver stage 22 to control the probe 10, the pulse signals and velocity estimation stages 110, 210 included in sub-systems 100 and 200.

In the transmission mode of the transmitter/receiver stage 22, the medium is scanned along the directions OZ of the excitation lines. In the receiving mode, the image of each excitation line is formed, taking into account the propagation time in the medium and the amplitude of the echoes returned by the obstacles encountered along the excitation line considered. In the transmission mode of the transmitter/receiver stage 22, each excitation line of the probe 10 thus provides acoustic high-frequency signals referenced 21 which enable the formation of a sequence of intensity images referenced 31 by way of a stage of image formation 32. The intensity image sequence is referred to as ultrasonic grayscale image sequence 31, which is displayed in the form of a 2-D image whose each column, called line, contains the information of one excitation line. So, the 2-D image contains a predetermined number of lines representing a segment of artery of about 28 mm.

Figure 3:
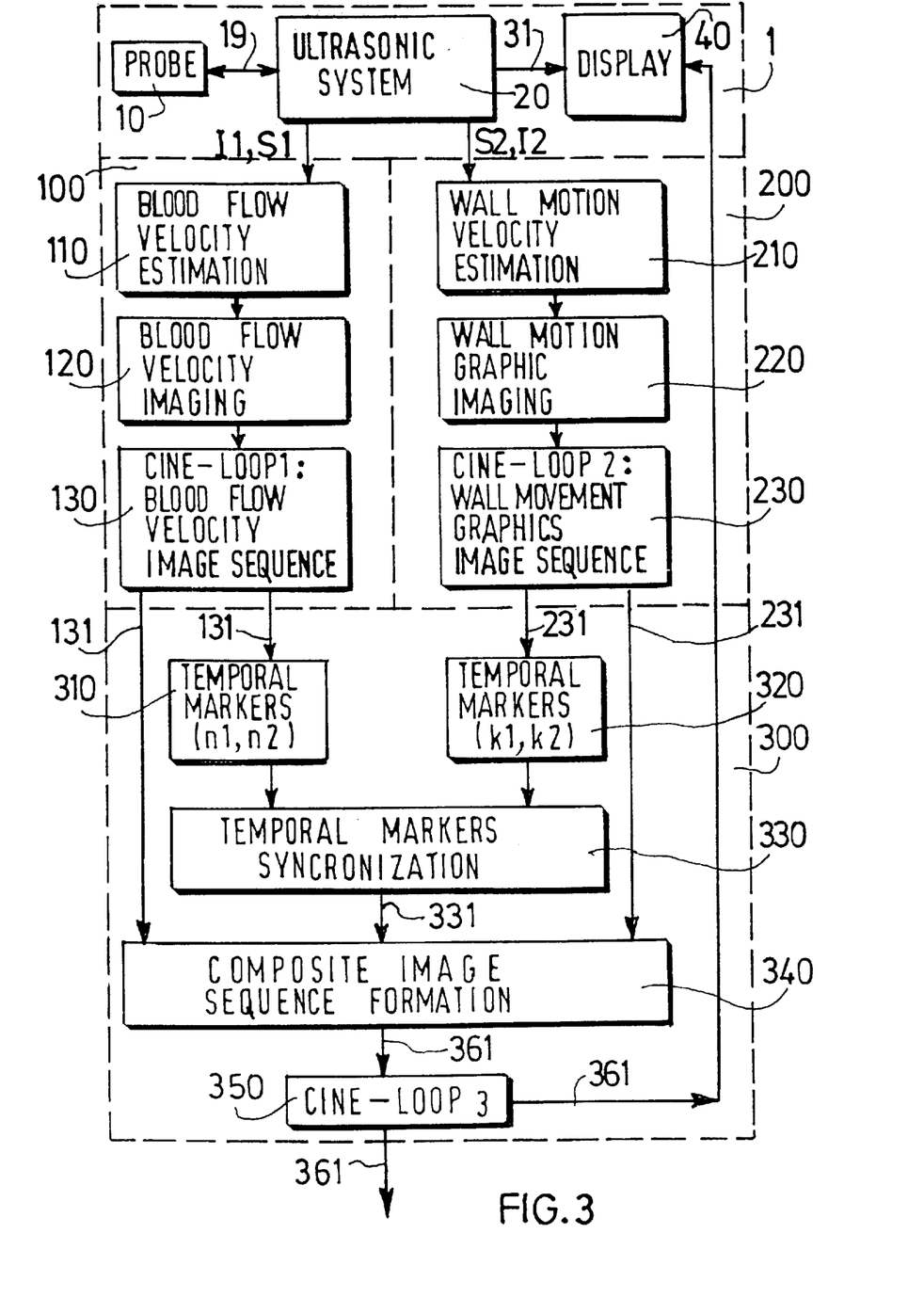
FIG. 3 shows a detailed block diagram of the ultrasonic diagnostic imaging system.
Figure 4:
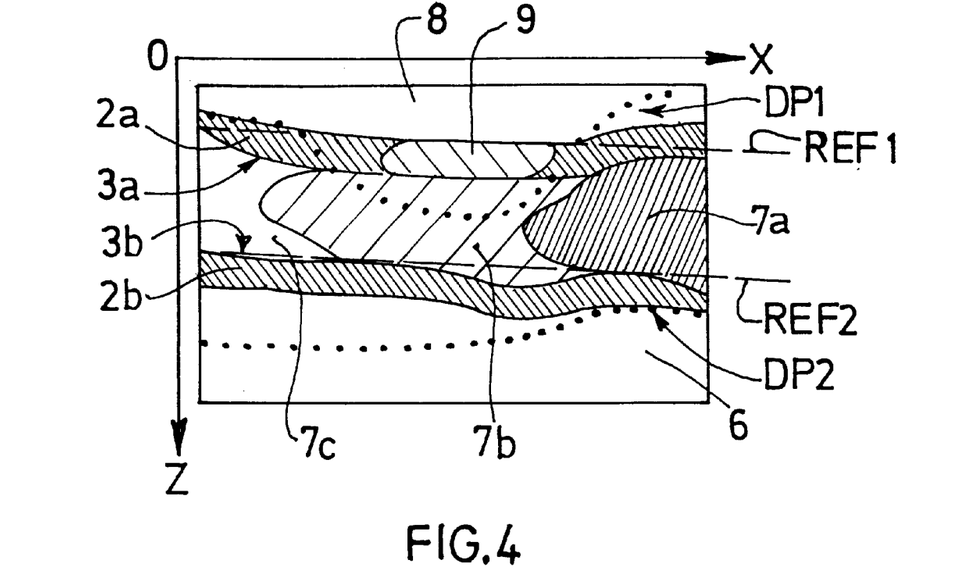
FIG. 4 shows a color-coded blood flow velocity image of an artery with superimposed graphic lines schematically representing wall movements.

Referring to FIG. 3, the ultrasonic diagnostic imaging system constructed in accordance to the principles of the present invention is shown in a detailed block diagram form. The ultrasonic diagnostic imaging system 1 is provided with:

a first sub-system or first means 100 for providing a first sequence 131 of color-coded blood flow velocity images of an artery;

a second sub-system or second means 200 for providing a second image sequence 231 of graphic lines representing the artery wall movements and with a third sub-system or third means 300 for synchronizing the images of the first and second sequences and providing a further third composite sequence of images 361 constituted of color-coded blood flow velocity images on which graphic lines representing the wall movements are superimposed.

The first, second and third means, respectively 100, 200, 300, may be programmed computer means, which are able to carry out steps of a method described hereafter with the same results as first, second and third sub-systems respectively. Referring to FIG. 3, the subsystems 100 and 200 have computation means that are of the same kind, however applied on signals that are different. It is also to be noted that the first sub-system acquires a first set of data at a first rate so that this first set of data is appropriate to be processed for providing an image sequence of blood flow velocity ($V_1$). The first rate is of the order of 30 images per second for example. Besides, the first sub-system acquires a second set of data at a second rate so that this second set of data is appropriate to be processed for providing an image sequence of wall motion velocity ($V_2$). The second rate is of the order of 200 images per second.

Referring to FIG. 3, the first ultrasonic sub-system 100 is coupled to the standard ultrasonic system 1 in order to permit operation thereof in a color coded velocity imaging mode which enables determination of the blood flow velocities in different parts of the segment of artery. To that end, this first ultrasonic sub-system 100 comprises:

a blood flow estimation stage 110, a blood flow velocity imaging stage 120 and a memory Cine-Loop 1 storing an image sequence 131.

Still referring to FIG. 1, for the estimation of blood flow velocity, which velocity is longitudinal, meaning parallel to the X'X-axis, the scanning of the medium by the ultrasonic probe is performed in such a manner that the artery is scanned forming an angle with said longitudinal X'X-axis. This permits of evaluating the arterial blood flow velocity based on the evaluation of the longitudinal velocity value component obtained by projection onto the OZ-axis, taking said angle into account. The behavior of the artery must be observed over a full cardiac cycle. Therefore, a sequence of a total number N of images covering a time interval that is at least equal to a cardiac cycle must be formed, the images being produced at each instant n, and N being a number superior to 1. So, time markers that are common to the blood flow velocity image sequence and to the cardiac cycle must be identified and are denoted hereafter starts of successive cardiac cycles n1, n2, n3 . . . Thus, the blood flow in the artery may be observed in relation to the various phases of the cardiac cycle.

The blood flow estimation stage 110 performs the processing of the high-frequency signals 21 issued by the emitter/receiver stage 22. Said high-frequency signals 21 denoted $S_1(X,Z,n)$ are produced by the transmitter/receiver stage 22 at the first rate appropriate to the formation, as a function of the instant n, of said N images of a blood flow velocity image sequence. The corresponding grayscale image sequence 31 issued by the grayscale image formation stage 32 at said first rate is based on intensity signals denoted $I1(X,Z,n)$. This blood flow estimation stage 110 performs a blood flow velocity estimation by estimating blood flow parameters that may be estimated in any way known of those skilled in the art. For example, these parameters may be provided by a CVI or by a Doppler embodiment.

A first imaging technique called CVI (from Color-coded Velocity Imaging) measures blood flow velocity directly by using time domain processing. CVI tracks individual clusters of blood cells using ultrasound to measure the distance and the time traveled. CVI is based on the principle of signature recognition. In a time domain correlation process, a first echo is stored in a digital memory. The shape of signal traces the relative position of blood cells, which is called ultrasound signature of the cluster. Some microseconds later, a second echo signal is stored. A computing system analyzes the two signal signatures by time shifting these two signatures until they match perfectly. This time shift is directly related to the distance the blood cells have moved, using the speed of sound in tissue. Blood-cell velocity is obtained by dividing this measured distance by the time between the two corresponding ultrasound pulses. It is to be noted that CIV measures peak velocities. Correction of the cosine angle between the vessel axis and the ultrasound beam is performed and the velocity computations are coded in shades of red and blue.

In the first embodiment based on CVI technique, the blood flow estimation stage 110 first performs a fixed echo suppression operation for suppressing echoes that are considered fixed, notably those caused by reflection of the ultrasound waves from the arterial walls in which the blood flow being studied occurs. The presence of said fixed echoes must be eliminated because their amplitude is much higher, about 40 dB in the case of arterial walls, than that of the signal useful for determining blood flow velocity, that is to say the signals which are returned by moving clusters of blood cells. Said blood flow estimation stage 110 further estimates said blood flow parameters. On the basis of signal differences between two successive excitation lines which are successively supplied by the fixed echo suppression operation, the blood flow velocity estimation stage 110 supplies correlation function values, and on the basis on these values, said blood flow velocity estimation stage 110 supplies parameters which characterize the different flow velocities encountered along the axis of propagation of the ultrasound wave. These parameters are the axial components of the blood flow local mean velocity $V_1(Z,X,n)$ at a given depth location along the OZ axis of propagation. In the blood flow estimation stage 110, the correlation function computation is controlled by a sequencer of the transmitter/receiver stage 22 and is preferably performed by 1-bit correlators which offer the advantage that the principal correlation peak obtained is triangle-shaped which is suitable for linear interpolation. The correlation functions or the formation of the mean value thereof are supplied to an interpolator which may be formed by a microprocessor or a table that enables the reconstruction of the principal correlation peak. The abscissa of said correlation peak enables the determination of the local velocity $V_1(Z,X,n)$ at a given depth in the medium that is stored.

In the first embodiment CVI, the image formation stage 120 processes the velocity values $V_1(Z,X,n)$ of the blood flow together with the images of the sequence of grayscale images 31, or intensity images $I_1(X,Z,n)$, formed at said first rate in the image formation stage 32 of the standard ultrasonic system 20. The velocities are color-coded in different colors and in several hues of said colors for indicating ranges of velocity and levels of velocity in the range, and maps of the color-coded velocities are superimposed unto respective grayscale images so as to forming a color-coded blood flow velocity image sequence.

A second imaging technique called Doppler is already used in numerous ultrasonic systems to calculate blood flow velocity indirectly by measuring the frequency shift and the phase shift variations from the original transmitted frequency pulse of a Doppler transducer. These shifts are caused by movement of blood cell clusters. Doppler velocity determination is based on mean velocities Correction of the cosine angle between the vessel axis and the ultrasound beam is performed and the velocity computations are color-coded.

In the second embodiment based on the Doppler technique, the blood flow estimation stage 110 processes Doppler echo signals issued by stage 20 of the ultrasonic sub-system 1, to obtain Doppler shift characteristics such as frequency corresponding to velocity and Doppler power corresponding to intensity. A Doppler processor processes an ensemble of two or more received echo sequences from a same spatial location of the artery and determines the Doppler phase or frequency shift. The Doppler processor may estimate the Doppler shift by a fast Fourier transform (FFT) or auto-correlation operation. Preferably the Doppler estimator employs two-dimensional auto-correlation which performs auto-correlation in both time and space and produce precise, highly resolved Doppler shift estimates. The Doppler estimator operates using a wall filter that removes low frequency tissue signal components from the echo signals to process and display only blood flow information. The operation of the wall filter is performed by a pass-band providing a cutoff frequency or velocity for example in the range of 50 Hz to 500 Hz, above which the Doppler frequencies generally correspond to blood flow velocities. For color flow imaging, the wall filter is employed to eliminate signals below this blood flow signal pass-band. The echoes returning from tissue would generally be found in the lower frequency pass-band below the 50–500 Hz cutoff.

In the Doppler embodiment, the blood flow velocity imaging stage 120 processes the segmented blood flow signals, which may include scan conversion to the desired image format, if needed. Said signals are color mapped to a range of color values. The color map of Doppler signals may then be overlaid on the grayscale map provided by stage 32 of the ultrasonic sub-system 1 using a video processor.

For the CVI embodiment as for the Doppler embodiment, the colors indicating the velocities, are superposed on the grayscale images of intensity 31 thus forming a color-coded blood flow velocity sequence of images referred to as 131. This color-coded blood flow velocity sequence 131 is further stored in a memory 130 labeled Cine-Loop-1.

Figure 5:
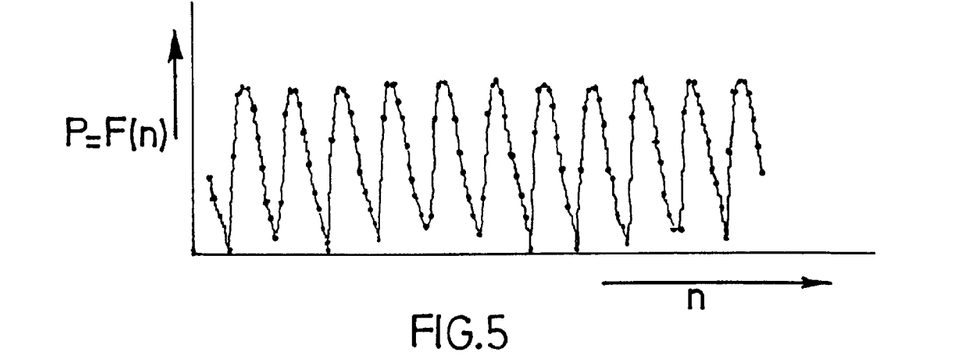
FIG. 5 shows a curve of a function F(n) representing the number of colored points in a color-coded velocity image in function of the instant n of said image in a sequence.

Referring to FIG. 3 and FIG. 5, the second ultrasonic sub-system 200 is coupled to the standard ultrasonic system 1 in order to permit of operating in a graphic mode which enables determination of the arterial wall velocity perpendicular to the direction of the blood flow at instants during a cardiac cycle, while the pulsating wave propagates within the artery considered as a wave-guide, and which enables construction of graphics reproducing the movements of said arterial walls for comfortable observation of their behavior. The second echographic subsystem 200 is implemented especially for compliance with the range of parietal displacements. The artery segment of the medium 6 studied is scanned two-dimensionally, as quickly as possible, and the temporal correlation operation 230 is performed one image after the other in the sequence of N images. The maximum parietal velocity is of the order of 10 mm/s. Consequently, an image period must be of the order of ≈7.5 ms. The number of excitation lines per image may be, for example x=68 or x=112, with a scanning step (distance between excitation lines) of 0.5 mm or 0.25 mm, which enables visualization of an arterial segment of 28 mm. The delay between the signals corresponding to each excitation line of the image may be adjusted by increasing or decreasing the number of excitation lines and the distance between the excitation lines. A memory may preferably be available at the input of the wall velocity estimation stage 210 for providing the necessary delay between two correlated signals.

This second ultrasonic sub-system 200 includes processing stages that execute steps of forming a sequence of images representing an artery segment and of computing the pattern of graphic lines DP1, DP2 reproducing the movements of the internal parietal boundaries 3a, 3b of said artery segment scanned by the probe 10 in the medium 6, at each scanned point of the parietal boundaries and at given instants n of a cardiac cycle, in conformity with a predetermined spatial amplification scale. These graphic lines fulfil the purpose of enabling the diagnosis of parietal lesions 9, based on the shape and amplitude of the parietal displacements with respect to the normal.

So, this second sub-system 200 comprises:
a wall motion estimation stage 210,
a wall motion graphic imaging stage 220
and a memory denoted Cine-Loop 2 storing an image sequence 231.

Still referring to FIG. 1, now for the estimation of the velocity of the arterial walls, which velocity is radial, the scanning of the medium by the echographic probe 10 is performed in such a manner that the artery is scanned longitudinally in the direction of its longitudinal X'X axis and that the excitation lines are considered orthogonal to the X'X axis in order to produce longitudinal cross-sectional intensity images of the artery, enabling the visualization of the front wall 2a and the rear wall 2b. The images provided by the excitation lines of direction OZ are the columns of each 2-D image that are formed by that method. The wall motion estimation stage 210 performs the processing of high-frequency signals 21 denoted $S_2(x,z,k)$ issued by the emitter/receiver stage 22 at the second rate compatible with the determination of the wall movement velocity. Here, k is the instant or the number of the signal in a set of signals, which are acquired at this second rate. From this set of signals, the ultrasonic sub-system 1 also provides a sequence of intensity images or grayscale image sequence denoted $I_2(x,z,k)$ that is formed in stage 32. Under the influence of the pulsating wave, the arterial walls 2a, 2b are subject to a periodic radial movement whose amplitude and velocity must be determined. Depending on the arterial wall state, the pressure variations induced by the pulsating wave create either a uniform arterial dilation or a distorted parietal movement. The behavior of the artery must be observed over a full cardiac cycle. Therefore, a sequence of a total number N of images covering a time interval which is at least equal to a cardiac cycle must be formed, N being a number superior to 1. Time markers that are common to the image sequence and to the cardiac cycle must be identified. These time markers are denoted start points n1, n2 of the cardiac cycle. So, the behavior of the arterial walls may be observed in relation to the various phases of the cardiac cycle.

In the sub-system 200, the velocity and the amplitude of the displacement of the walls are first determined in a wall velocity estimation stage 210 that performs a temporal correlation operation. During this temporal correlation operation, the successive ultrasonic echoes, produced by the motion of tissue structures and generated in the transmitter-receiver stage 22 of the standard ultrasonic system 20, are compared by way of their correlation functions. The displacement of the tissue structures from one ultrasonic emission to the next is estimated while taking into account the displacement of the correlation peak corresponding to the delay introduced by this displacement upon reception. The correlation operation of stage 210 provides velocity measurements in the form of a second sequence of two-dimensional velocity images denoted $V_2(X,Z,k)$. Then, in the wall motion estimation stage 210, during an operation called post-processing, the parietal movements are localized for determining the locations of the arterial walls in corresponding echo amplitude images $A_2(X,Z,k)$ that are formed by an operation of measuring the amplitudes of echoes, and for transferring the locations of the arterial walls in the arterial wall velocity images. In stage 210, during said post-processing operation, an adaptable threshold is further calculated and applied to each amplitude image 111 $A_2(X,Z,k)$ in order to produce digital amplitude images in which the transitions corresponding to the internal parietal boundaries are further smoothed by filtering. The post-processing operation of stage 210 subsequently includes an operation of detection of internal parietal boundaries 3a, 3b. The image is thus scanned along the excitation lines of direction OZ in order to detect the points situated on these boundaries. The post-processing operation also includes evaluation of parietal displacement values denoted D1 and D2 of respectively upper and lower walls 2a, 2b. For each line having a co-ordinate X on the X'X-axis of each image n of the image sequence, the displacements D1 and D2 are calculated by determining instantaneous mean velocities of said walls. The resultant wall displacements are processed so as to determine the temporal markers k1, k2 . . . of the cardiac cycle at which said displacements are zero. This permits of determining reference positions REF1, REF2 corresponding to the starts of the cardiac cycles derived from the parietal boundaries extracted from the amplitude images.

Referring to FIG. 3 and to FIG. 5, the stage 220 of wall motion graphic imaging performs the encrustation, or graphic superposition, in each image k in the sequence of K intensity images $I_2(Z,X,k)$ provided by the image formation stage 32 of the sub-system 1 at said second rate, of:

reference lines REF1, REF2 corresponding to the starts of cardiac cycles;

graphic lines DP1, DP2 which represent the displacements D1 and D2 of the points of the parietal boundaries at each instant k, so as to simulate the movements of the front and rear arterial walls respectively.

The encrusted images referred to as 231 that are provided by the stage of wall motion graphic imaging 220 are then stored in the memory 230 labeled Cine-loop-2.

Referring to FIG. 3, the first sub-system 100 and the second sub-system 200 are further connected to a third sub-system 300, which has means for providing the instants of the starts of the cardiac cycles referred to as temporal markers that are accurately identified. Said third sub-system 300 has first means for providing first temporal markers denoted n1, n2, n3 . . . in the first sequence of N color-coded blood flow velocity images and has second means for providing second temporal markers denoted k1, k2, k3 . . . in the second sequence of K arterial wall motion images. To that end, said third sub-system 300 comprises:

a first stage 310 of detection of the first temporal markers in the first sequence of N color-coded images of blood flow velocity;

a second stage 320 of detection of the second temporal markers in the second sequence of K images incrusted with graphic lines representing the arterial wall motion;

a third stage 330 of synchronization of the first and second temporal markers;

a fourth stage 340 of construction of a composite image sequence formed of a color coded blood flow velocity image sequence with encrusted graphics representing wall motion;

and a memory labeled Cine-Loop 3 to store said composite image sequence denoted 361.

So, the first stage 310 comprises the determination of temporal markers relating to the sequence of N blood flow velocity images. It is wanted to determine at least a first temporal marker n1 and a second temporal marker n2 for this sequence, so a number of blood flow images greater than N is constructed. To determine the first temporal markers, the first stage 310 comprises an operation of construction of a curve, shown in FIG. 5, whose each point is constituted by the number $P_n$ of colored points evaluated in each 2-D color-coded image, at each corresponding instant n, of the constructed blood flow velocity images, so as: $P_n=F(n)$. It is to be noted that the color-coded blood flow velocity image sequence 131, which is stored in Cine-Loop 1, is constituted from a first plan of the grayscale images 31 formed at each instant n, upon which a second plan of the color map of blood flow velocity values is superimposed. So, the first stage 310 of cardiac cycle detection operates the counting of the number $P_n$ of the colored points that are in each of the color maps, at each instant n. This number $P_n$ represents the volume of blood at said instant n in the segment of artery of the color-coded image. For performing the counting, each colored point that pertains to the color map in the upper plan, is given a value equal to 1, while each other point that pertains uniquely to the grayscale lower plan, is given the value zero. Then, each 2-D image is processed by scanning the image points and adding the values found at those image points for constructing one point of the curve F(n) per 2-D image. In the case, for example, when the sequence of 2-D images is formed at a rate of 15 images per second, the curve F(n) may be constructed with about 15 points per cardiac cycle, said cardiac cycle being of about one second.

It has been observed, according to the present invention that the curve F(n) shows minimum points regularly spaced in function of the instants n, which minimum points correspond to the start points of the cardiac cycle. So, according to the present invention, these minimum points of the curve F(n) are determined in order to provide corresponding temporal markers n1, n2, n3 . . . of the blood flow velocity image sequence 131.

Figure 6:
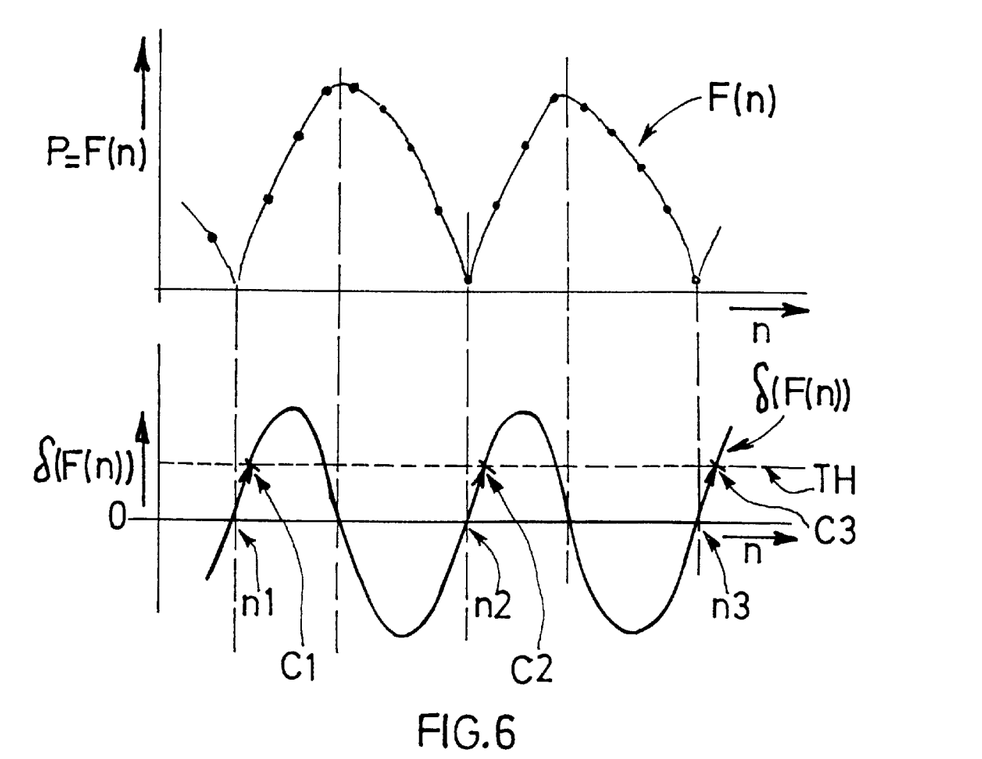
FIG. 6 shows the curve F(n) together with the derivative δ[F(n)] of said curve.

Referring to FIG. 6, a simplified representation of the curve F(n) is shown together with a representation of the curve of the first derivative δ(n) of the function F(n) given by:

δ(n)=F(n)−F(n−1). The evaluation of the derivative δ(n) permits of determining the minimum points n1, n2, n3, . . . of the curve F(n). The curve of the derivative δ(n) crosses the value zero each time that the function F(n) has a minimum and each time that said function F(n) has a maximum. Only the minimum value positions in function of n are interesting in order to determine the temporal markers. So, a positive threshold TH is designed on the curve of the derivative δ(n), and based on said threshold, the interesting zero points of the derivative δ(n) are determined and retained as temporal markers when they start an increasing positive part of the curve δ(n) that crosses the threshold line TH.

Now, the second stage 320 comprises the determination of temporal markers relating to the sequence of K wall motion images. It is wanted to determine at least a first temporal marker k1 and a second temporal marker k2 for this sequence, so a number of blood flow images greater than K is constructed. To determine the second temporal markers, the second stage 320 comprises an operation of construction of a curve, shown in FIG. 7, whose each point is constituted by the mean dilation D(k) in each 2-D wall motion image, at each corresponding instant k, of the constructed wall motion image sequence 231 issued from the memory Cine-Loop 2. The temporal markers are determined by analysis of the temporal variations of said mean arterial dilation along the longitudinal arterial axis X'X. This mean dilation D(k) is calculated as the difference between the displacements of the two walls 2a, 2b, integrated from the co-ordinate X=0 to the co-ordinate $X=X_{max}$ in the longitudinal direction of the segment of artery in the 2-D image at the instant k.

Figure 7:
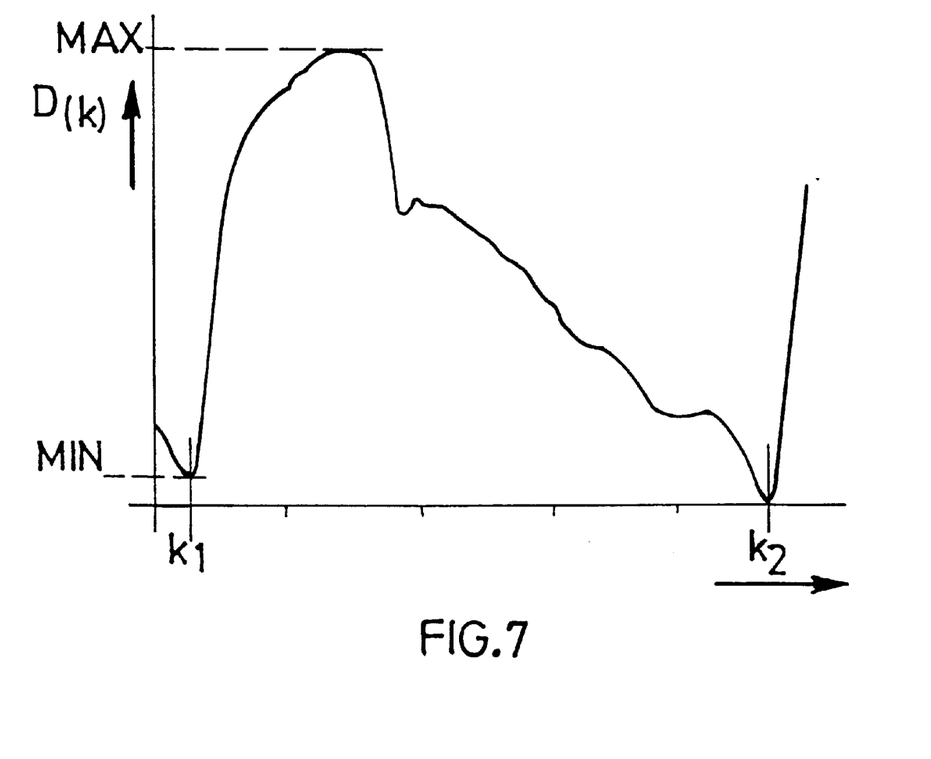
FIG. 7 shows a curve of parietal mean displacements D(k) of an artery as a function of temporal instants k.

Referring to FIG. 7, the curve D(k) shows minimum values at abscissae k1 and k2, which must be identified as starts of cardiac cycles by means of an automatic method. To this end, the minimum and maximum values MIN and MAX are detected on the curve of FIG. 7 and a function g(k) is calculated on the basis of this detection, so as:

If $[D(k)-MIN]/(MAX-MIN)>D_0$, then g(k)=0

Else, g(k)=1.

Consequently, the function g(k) validates the segments of the curve D(k) which are below a predetermined threshold denoted $D_0$. On each of these segments, the minimum values of D(k) are determined and the corresponding instants k1, k2 are stored as the starts of successive cardiac cycles.

The third stage 330 performs the synchronization between the markers n1, n2 relating to the blood flow velocity image sequence and the markers k1, k2 relating to the wall motion image sequence. Each wall motion image formed at a given instant k, between k1 and k2, must moreover be synchronized with a corresponding blood flow velocity image formed at a corresponding instant n, between n1 and n2, such as:

k1 corresponds to n1, and k2 corresponds to n2, k corresponds to n, with k1≦k≦k2 and n1≦n≦n2. Thus, when defining a proportionality factor denoted α, the correspondence between the values of n and the values of k are given by the relations:

k2−k1=α(n2−n1), and: k−k1=α(n−n1)

from which: α=(k2−k1)/(n2−n1) and k=α(n−n1)+k1 k=[(k2−k1)/(n2−n1)](n−n1)+k1

The fourth stage 340 of composite image sequence formation receives this value of k that is an information referred to as data 331, which permits of synchronizing the first sequence of images 131 at a first rate stored in the memory Cine-Loop-1 and of the second sequence of images 231 at a second rate stored in the memory Cine-Loop-2 and of superposing these images for providing a composite sequence denoted 361 of color-coded blood flow velocity images having encrusted wall movement graphics.

This composite image sequence 361 is subsequently stored in a memory labeled Cine-Loop-3. The image sequence 361 which is stored in Cine-Loop 3 may be formed at a third rate with respect to the first and second sequences of Cine-Loop 1 and Cine-Loop 2 but is formed preferably at the lower rate of the two rates of acquisition of data, for example 30 images per second, which is sufficient for display.

During the display of the composite sequence 361 by the display device 40, the physician can qualitatively and quantitatively evaluate the distortions or non-distortions of the graphic lines simulating the displacements of the arterial walls together with the blood flow velocity which is color-coded. The physician may derive therefrom the presence and the seriousness of stenosis, or elasticity defects, linked to the arterial walls of the subjacent blood flow velocity image. The visualization of the arterial dilation in real time, together with the blood flow velocity enables optimization of the position of the echographic probe 10 so as to obtain a cross-sectional plane which passes through the arterial axis parallel to X'X.

The invention has been described in relation to the processing of echographic signals, but can also be applied to the processing of signals of a different nature: electric, electromagnetic, etc.

What is claimed is:

1. An ultrasonic image processing method for displaying a composite sequence of images of an artery segment with indication of blood flow velocity and wall movements in function of the cardiac cycle, comprising steps of:

forming, at a first rate, a first sequence (131) of blood flow velocity color-coded images and forming, at a second rate, a second sequence (231) of images with wall movement graphics;

constructing said composite image sequence (361) by determining a first set of temporal markers (n1,n2), related to the cardiac cycle, in the first image sequence as the minimum points of a curve (P(n)) of the number of the colored points per image in function of the image instants, determining a second set of temporal markers (k1,k2), related to the same cardiac cycle, in the second image sequence as the minimum points of a curve (D(k)) of the arterial mean dilation in function of the image instants, and by superposing the first and second image sequences by synchronizing the respective markers of said two sets, and displaying the composite image sequence.

2. An ultrasonic image processing method as claimed in claim 1, comprising steps of forming, at said first rate, the first sequence (131) of blood flow velocity color-coded images by forming a sequence (31) of ultrasonic grayscale images and a sequence of blood flow velocity color-coded maps (110) and steps of superposing the color-coded maps unto the grayscale images at each image instant (n).

3. An ultrasonic image processing method as claimed in claim 2, comprising steps of determining the blood flow color-coded map using a CVI blood flow velocity estimation technique (110).

4. An ultrasonic image processing method as claimed in claim 2, comprising steps of determining a blood flow color-coded map using a Doppler blood flow velocity estimation technique (110).

5. An ultrasonic image processing method as claimed in claims comprising, for determining said first set of temporal markers (n1,n2), steps of counting the numbers of the colored points in the color-coded maps in the respective sequence images at every image instants, for forming, with said numbers, the points of the curve (P(n)) of the number of the colored points per image in function of the image instants and for determining the minimum points of said curve (n1,n2) as temporal markers.

6. An ultrasonic image processing method as claimed in claim 1 comprising steps of calculating the first derivative of the curve (P(n)) of the number of the colored points per image in function of the image instants, and for determining the minimum points (n1,n2) of the curve (P(n)) as zero points on increasing parts of the first derivative.

7. An ultrasonic image processing method as claimed in claim 1 comprising steps of forming, at said second rate, the second sequence (231) of images with wall movement graphics by forming a sequence (31) of ultrasonic grayscale images and a sequence of images of wall motion graphics (210) and steps of superposing the wall motion graphics unto the grayscale images at each image instant (k).

8. An ultrasonic image processing method as claimed in claim 1 comprising, for determining said second set of temporal markers (k1,k2), steps of determining, at each image instant, based on the arterial wall position, the mean dilation (D(k)) of the artery, for forming a curve (D(k)) of the arterial mean dilation in function of the image instants and for determining the minimum points (k1,k2) of said curve as temporal markers (k1,k2).

9. An ultrasonic image processing method as claimed in claim 1 comprising, for synchronizing the first and second image sequences, steps of determining the image instants (k) of the images of the second sequence, which correspond to the image instants (n) of the images of the first sequence.

10. An ultrasonic examination system having an ultrasonic standard system connected to a probe to acquire ultrasonic data and a display system to display a composite sequence of images of an artery segment with indication of blood flow velocity and wall movements in function of the cardiac cycle, said ultrasonic examination system comprising, for carrying out a method as claimed in claim 1 a first sub-system for forming, at a first rate, a first sequence (131) of blood flow velocity color-coded images and a second sub-system for forming, at a second rate, a second sequence (231) of images with wall movement graphics, and comprising a third sub-system for determining in the first image sequence a first set of temporal markers (n1,n2) as the minimum points of a curve (P(n)) of the number of the colored points per image in function of the image instants, determining in the second image sequence a second set of temporal markers (k1,k2) as the minimum points of a curve (D(k)) of the arterial mean dilation in function of the image instants, and constructing said composite image sequence (361) by superposing the first and second image sequences by synchronizing the respective markers of the first and second sets.

11. A computer program product comprising a set of instructions for carrying out the method as claimed in claim 1.

* * * * *